US012575736B2

(12) United States Patent
Kim et al.

(10) Patent No.: US 12,575,736 B2
(45) Date of Patent: Mar. 17, 2026

(54) METHOD AND SYSTEM FOR ESTIMATING PHYSIOLOGICAL INFORMATION VIA SET OF LEDs AND PHOTODETECTORS BY DETERMINING A CORRECTION PROFILE BASED ON A RATIO

(71) Applicant: MEDITHINGS CO., LTD., Seoul (KR)

(72) Inventors: Sehwan Kim, Seoul (KR); Aram Kim, Seoul (KR); Hou Lam Jesse, Seoul (KR)

(73) Assignee: MEDITHINGS CO., LTD., Seoul (KR)

( * ) Notice: Subject to any disclaimer, the term of this patent is extended or adjusted under 35 U.S.C. 154(b) by 0 days.

(21) Appl. No.: 18/775,098

(22) Filed: Jul. 17, 2024

(65) Prior Publication Data

US 2025/0031973 A1     Jan. 30, 2025

(30) Foreign Application Priority Data

Jul. 18, 2023    (KR) ........................ 10-2023-0092976
Jul. 26, 2023    (KR) ........................ 10-2023-0097534
Oct. 16, 2023    (KR) ........................ 10-2023-0137670

(51) Int. Cl.
*A61B 5/00*          (2006.01)

(52) U.S. Cl.
CPC .......... *A61B 5/0075* (2013.01); *A61B 5/4872* (2013.01); *A61B 5/4875* (2013.01);
(Continued)

(58) Field of Classification Search
CPC ... A61B 5/0075; A61B 5/4872; A61B 5/4875; A61B 5/6823; A61B 5/7271;
(Continued)

(56) References Cited

U.S. PATENT DOCUMENTS 11,188,730 B1    11/2021  Kwon et al.
2016/0310054 A1*  10/2016  Izzetoglu ................. A61B 5/01
(Continued)

FOREIGN PATENT DOCUMENTS

EP          3275363 A1    1/2018
KR    10-2020-0119501 A   10/2020
(Continued)

OTHER PUBLICATIONS

Nov. 21, 2024—(EP) European Search Report—App. No. 24189118. 3.

(Continued)

*Primary Examiner* — Serkan Akar
(74) *Attorney, Agent, or Firm* — Banner & Witcoff, Ltd.

(57)          ABSTRACT

The present disclosure provides a method for estimating physiological information performed by at least one processor. This method may include: receiving, by photodiodes, a first optical data set associated with light irradiated by plural light emitting diodes (LEDs) to a first substance; receiving, by the photodiodes, a second optical data set associated with light irradiated by the plural LEDs to a second substance; calculating first correction data associated with the plural LEDs based on the first optical data set and the second optical data set; calculating second correction data associated with the plural LEDs based on the first correction data and profile data associated with the plural LEDs; and estimating physiological information associated with the second substance based on the first correction data and the second correction data.

13 Claims, 8 Drawing Sheets

(52) U.S. Cl.
CPC .......... *A61B 5/6823* (2013.01); *A61B 5/7271* (2013.01); *A61B 2560/045* (2013.01); *A61B 2560/0462* (2013.01); *A61B 2562/046* (2013.01)

(58) Field of Classification Search
CPC ...... A61B 2560/045; A61B 2560/0462; A61B 2562/046; A61B 5/1455; A61B 5/14546; A61B 2562/043; A61B 5/1495; A61B 5/443; A61B 2560/0233
See application file for complete search history.

(56) References Cited

U.S. PATENT DOCUMENTS

| | | | |
|---|---|---|---|
| 2017/0319131 A1* | 11/2017 | Xavier Da Silveira | .................... A61B 5/14546 |
| 2018/0192929 A1 | 7/2018 | Scheele et al. | |
| 2020/0323437 A1 | 10/2020 | Lee et al. | |
| 2021/0356322 A1 | 11/2021 | Nam et al. | |

| | | | |
|---|---|---|---|
| 2022/0107220 A1 | 4/2022 | Kim et al. | |
| 2023/0141246 A1 | 5/2023 | Jung et al. | |
| 2023/0146917 A1 | 5/2023 | Eom et al. | |
| 2023/0324293 A1 | 10/2023 | Lee | |

FOREIGN PATENT DOCUMENTS

| | | | |
|---|---|---|---|
| KR | 10-2021-0142304 A | 11/2021 | |
| KR | 10-2022-0030089 A | 3/2022 | |
| KR | 10-2023-0068639 A | 5/2023 | |
| KR | 10-2023-0068694 A | 5/2023 | |
| KR | 10-2023-0146347 A | 10/2023 | |

OTHER PUBLICATIONS

Lam et al., "Spectral correction of light emitting diodes enables accurate hydration ratio calculation using narrowband diffuse reflectance spectroscopy", Journal of Biomedical Optics, SPIE, 1000 20th St. Bellingham WA 98225-6705 USA, vol. 28, No. 7, Jul. 1, 2023), pp. 75005-1-75005-9.

* cited by examiner

700

METHOD AND SYSTEM FOR ESTIMATING PHYSIOLOGICAL INFORMATION VIA SET OF LEDs AND PHOTODETECTORS BY DETERMINING A CORRECTION PROFILE BASED ON A RATIO

CROSS-REFERENCE TO RELATED APPLICATIONS

The present application claims priority to and the benefit of Korean Application No. 10-2023-0092976, filed on Jul. 18, 2023, No. 10-2023-0097534, filed on Jul. 26, 2023, and No. 10-2023-0137670, filed on Oct. 16, 2023, in the Korean Intellectual Property Office, the entire disclosure of which is incorporated by reference herein.

FIELD

The present disclosure relates to a method and system for estimating physiological information and, more particularly, to a method and system for accurately estimating physiological information by correcting optical data of the body.

BACKGROUND

Maintaining hydration is essential for human survival, but monitoring it in a continuous and portable manner using an optical method may be difficult. Dehydration corresponding to a body water loss of 10 percent may cause severe decline in motor and cognitive function, and further loss of body water may lead to death. Likewise, tissue hydration in the body may be an important biomarker in other fields such as breast cancer research, dermatology, and critical care medicine. In related-art techniques, near-infrared (NIR) optical technology such as diffuse optical spectroscopy or spatial frequency domain imaging (SFDI) has been used to estimate the water content.

Additionally, in related-art techniques, narrowband diffuse reflectance spectroscopy (nb-DRS) has been demonstrated as being usable to calculate the hydration ratio (or $RH_2O$), which closely tracks the absolute water fraction. This can be confirmed by analyzing the diffuse reflectance in the far-infrared region of wavelengths between 900 and 1000 nanometers by using a broadband lamp and a spectrometer. Here, $RH_2O$ may be defined as a ratio of water ($H_2O$) and lipid (FAT) as shown in Equation 1 below.

$$RH_2O \ (\%) = 100 \times \frac{H_2O}{H_2O + FAT} \qquad \text{[Equation 1]}$$

Meanwhile, nb-DRS may be suitable for miniaturization as a wearable hydration monitor due to its low hardware requirements. For light sources, multi-wavelength LEDs may be used as a smaller, lower-power, cheaper alternative to broadband lamps. However, when switching from a spectrometer to a photodiode to detect a light source, there is a limitation that high-resolution spectrum data is lost because the photodiode cannot process wavelength information. Additionally, since the LED has a full-width at half maximum (FWHM) that cannot be ignored, there is a problem that spectrum cross-talk may potentially occur.

SUMMARY

Embodiments of the present disclosure provide a method and system for estimating physiological information.

The present disclosure may be implemented in various ways, such as a method, a device (system), or a computer program stored in a readable storage medium.

According to an embodiment of the present disclosure, a physiological information estimation method may include: receiving, by photodiodes, a first optical data set associated with light irradiated by plural light emitting diodes (LEDs) to a first substance; receiving, by the photodiodes, a second optical data set associated with light irradiated by the plural LEDs to a second substance; calculating first correction data associated with the plural LEDs based on the first optical data set and the second optical data set; calculating second correction data associated with the plural LEDs based on the first correction data and profile data associated with the plural LEDs; and estimating physiological information associated with the second substance based on the first correction data and the second correction data.

According to an embodiment of the present disclosure, the first substance may be a substance whose reflectance information of light irradiated thereto is known in advance, and the second substance may be a test substance to be tested.

According to an embodiment of the present disclosure, calculating second correction data may include calculating normalized weight data associated with the plural LEDs based on the profile data associated with the plural LEDs.

According to an embodiment of the present disclosure, calculating second correction data may further include calculating simulated diffuse reflectance data associated with the plural LEDs based on the normalized weight data and a diffusion model.

According to an embodiment of the present disclosure, the diffusion model may be a model that predicts a diffuse reflectance for a light-irradiated medium based on a chromophore concentration and an extinction coefficient.

According to an embodiment of the present disclosure, calculating second correction data may further include calculating the second correction data based on the first correction data and the simulated diffuse reflectance data associated with the plural LEDs.

According to an embodiment of the present disclosure, calculating second correction data may further include calculating the second correction data by adjusting a scale of the simulated diffuse reflectance data based on a portion of the first correction data and a portion of the simulated diffuse reflectance data.

According to an embodiment of the present disclosure, the physiological information may include information about water ($H_2O$) and information about fat.

There may be provided a computer-readable non-transitory recording medium that stores instructions for executing the method according to an embodiment of the present disclosure on a computer.

According to an embodiment of the present disclosure, a user terminal is provided. The user terminal may include: a communication module; a memory; and at least one processor connected to the memory and configured to execute at least one computer-readable program stored in the memory, wherein the at least one computer-readable program may include instructions that are configured to receive, by photodiodes, a first optical data set associated with light irradiated by plural LEDs to a first substance, receive, by the photodiodes, a second optical data set associated with light irradiated by the plural LEDs to a second substance, calculate first correction data associated with the plural LEDs based on the first optical data set and the second optical data set, calculate second correction data associated with the plural LEDs based on the first correction data and profile data associated with the plural LEDs, and estimate physiological information associated with the second substance based on the first correction data and the second correction data.

According to some embodiments of the present disclosure, it is possible to estimate physiological information based on optical data obtained through a medical instrument. Additionally, the estimated physiological information may be provided to the user through a user terminal. In this way, the invention according to the present disclosure may provide physiological information to the user without the help of an expert such as a doctor. Further, the invention according to the present disclosure may be simple to use and highly convenient to the user and may be highly accessible to consumers through personalization.

According to some embodiments of the present disclosure, crosstalk may be reduced by more accurately estimating physiological information while using multi-wavelength LEDs and photodiodes. Thereby, simplification and miniaturization of spectroscopy technology may be promoted. Additionally, the method according to the present disclosure may be usefully applied to narrow-band LED-based devices such as wearable hydration monitors.

The effects of the present disclosure are not limited to those mentioned above, and other effects not mentioned may be clearly understood by those skilled in the art to which this disclosure pertains (referred to as "ordinary persons skilled in the art art") from the description of the claims.

BRIEF DESCRIPTION OF DRAWINGS

Embodiments of the present disclosure will be described with reference to the accompanying drawings described below, in which similar reference symbols indicate similar elements but without being limited thereto.

DETAILED DESCRIPTION

Figure 1:
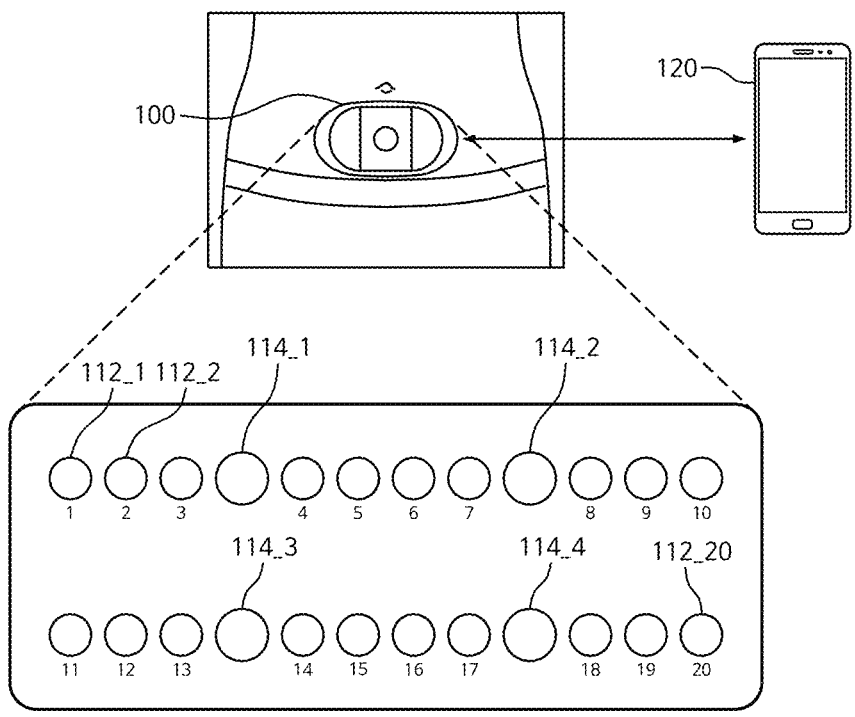
FIG. 1 is a schematic diagram showing an example of a medical instrument for estimating physiological information according to an embodiment of the present disclosure.

Hereinafter, specific details for carrying out the present disclosure will be described in detail with reference to the accompanying drawings. However, in the following description, detailed descriptions of well-known functions or configurations will be omitted if there is a risk of unnecessarily obscuring the gist of the present disclosure.

In the accompanying drawings, identical or corresponding elements are given the same reference symbols. Additionally, in the following description of the embodiments, repeated descriptions of identical or corresponding components may be omitted. However, even if a description of a specific component is omitted, it is not intended that such a component is not included in a corresponding embodiment.

Advantages and features of the disclosed embodiments and methods for achieving them will become clear by referring to the embodiments described below in conjunction with the accompanying drawings. However, the present disclosure is not limited to the embodiments disclosed below and may be implemented in various different forms, and these embodiments are provided only to make the disclosure complete and fully inform those skilled in the art of the scope of the invention.

Terms used in this specification will be briefly described, and the disclosed embodiments will be described in detail. The terms used in this specification are selected as being general terms currently widely used as much as possible while considering their functions in the present disclosure, but they may vary depending on the intentions of engineers working in the related fields, precedents, the emergence of new technologies, or the like. Additionally, there may be terms deliberately selected by the applicants, and in such a case, their meanings will be described in detail in the description of the relevant invention. Accordingly, the terms used in this disclosure should be defined based on the meanings of the terms and the overall content of the present disclosure, rather than simply the names of the terms.

In this specification, singular expressions include plural expressions, unless the context clearly indicates otherwise. Also, plural expressions include singular expressions, unless the context clearly indicates otherwise. In the entire specification, when a part includes a specific component, this means that other components may be further included rather than excluding other components unless expressly stated to the contrary.

In addition, the term 'module' or 'unit' used in the specification refers to a software or hardware component, and the 'module' or 'unit' performs specific roles. However, the 'module' or 'unit' is not limited to software or hardware. A 'module' or 'unit' may be configured to reside on an addressable storage medium and may be configured to drive one or more processors. Thus, as an example, a 'module' or 'unit' may include at least one of components such as software components, object-oriented software components, class components and task components, processes, functions, attributes, procedures, subroutines, program code segments, drivers, firmware, microcode, circuits, data, databases, data structures, tables, arrays, or variables. Components and modules or units may be combined into a smaller number of larger ones or may be divided into a larger number of smaller ones, while maintaining the same functionality.

According to an embodiment of the present disclosure, a 'module' or 'unit' may be implemented with a processor and a memory. The term 'processor' should be interpreted broadly to include a general-purpose processor, central processing unit (CPU), microprocessor, digital signal processor (DSP), controller, microcontroller, state machine, and the like. In some contexts, the 'processor' may refer to an application-specific integrated circuit (ASIC), programmable logic device (PLD), field programmable gate array (FPGA), or the like. The 'processor' may refer to, for example, a combination of a DSP and a microprocessor, a combination of plural microprocessors, a combination of one or more microprocessors coupled with a DSP core, or a combination of other processing devices. In addition, the term 'memory' should be interpreted broadly to include any electronic component capable of storing electronic information. The 'memory' may refer to various types of processor-readable media such as random access memory (RAM), read-only memory (ROM), non-volatile random access memory (NVRAM), programmable read-only memory (PROM), erasable-programmable read-only memory (EPROM), electrically erasable PROM (EEPROM), flash memory, magnetic or optical data storage, and registers. A memory is said to be in electronic communication with a processor if the processor can read information from the memory and/or write information to the memory. The memory integrated into a processor is in electronic communication with the processor.

In the present disclosure, the term 'system' may include, but not limited to, at least one of a server device and a cloud device. For example, a system may be composed of one or more server devices. As another example, a system may be composed of one or more cloud devices. As another example, a system may be configured to operate together with a server device and a cloud device.

In this disclosure, the term 'display' may refer to any display device associated with a computing device. For example, it may refer to a specific display device that is controlled by the computing device or is capable of displaying information/data provided by the computing device.

In the present disclosure, "each of a plurality of A's" may refer to each of all components included in plural A's or may refer to each of some components included in plural A's.

Light emitting diodes (LEDs) are commonly used in tissue spectroscopy due to their small size, low cost, and simplicity. However, LEDs are often assumed to be single-wavelength elements despite having a relatively wide spectral bandwidth. Additionally, when an LED is used together with a photodiode, the wavelength information of light detected by the photodiode may be lost. Because of this, calculation errors may occur when calculating the concentration of chromophores by using LEDs and photodiodes. In particular, these errors may be noticeable when analyzing water and fat in the 900-1000 nm range, where the spectral bandwidth of LEDs can cover most of the analysis region, which may result in serious cross-talk.

The present disclosure provides a spectral correction (SC) method for correcting the spectral bandwidth of an LED. The method of the present disclosure may be applied to a narrowband technique using LEDs with broad and overlapping spectra. Specifically, in the present disclosure, narrowband diffuse reflectance spectroscopy (nb-DRS), a technique that can quantify the hydration ratio ($RH_2O$) of turbid media, may be used. Generally, nb-DRS requires broadband light sources and a spectrometer. However, in this disclosure, the hardware is reduced to 5 LEDs and 1 photodiode and a spectral correction method is used to correct spectral crosstalk. The effectiveness of the spectral correction method of the present disclosure may be confirmed through simulations, emulsion phantoms, and tests on human tissue.

According to the simulation results, the spectral correction method of the present disclosure may correct the calculated $RH_2O$ error according to the spectral bandwidth of the LED. In addition, according to the emulsion phantom results, an average error of 8.7 percent (maximum error of 14 percent) may occur when the spectral correction method of the present disclosure is not used. On the other hand, when the spectral correction method of the present disclosure is applied, the average error may be reduced to 2.2 percent (maximum error of 6.4 percent). As such, despite using multiple LEDs with very wide and overlapping spectra, the spectral correction method of the present disclosure may restore the performance of the narrowband method to a level similar to that of a much larger full broadband system.

By providing an algorithm for spectral correction, the present disclosure can mitigate crosstalk in narrowband technologies even when using multiple LEDs with broad and overlapping spectra. The effects of the present disclosure can be demonstrated through simulations, emulsion phantoms over a wide range of $RH_2O$ values, and tests on human tissue (e.g., human abdomen, thenar tissue). The spectral correction method of the present disclosure may facilitate the development of tissue hydration monitors using nb-DRS and may be applied to other modalities.

FIG. 1 is a schematic diagram showing an example of a medical instrument 100 for estimating physiological information according to an embodiment of the present disclosure. As shown, the medical instrument 100 may include a communication unit to perform transmission and reception with a user terminal 120. Additionally, the medical instrument 100 may include a plurality of photodiodes 112_1 to 112_20 and a plurality of light source groups 114_1 to 114_4. The medical instrument 100 may obtain optical data related to the body by using the plural photodiodes 112_1 to 112_20 and the plural light source groups 114_1 to 114_4. The user terminal 120 may receive optical data related to the body and estimate the user's physiological information based on the received optical data. In FIG. 1, the medical instrument 100 is shown as including 20 photodiodes 112_1 to 112_20 and 4 light source groups 114_1 to 114_4, but without being limited thereto. That is, the number of photodiodes and the number of light source groups included in the medical instrument 100 may be changed as needed.

In an embodiment, the plural photodiodes 112_1 to 112_20 and the plural light source groups 114_1 to 114_4 may be disposed on one surface of the medical instrument 100. In this case, the medical instrument 100 may be attached to the body so that the corresponding surface faces the body. In an example, the medical instrument 100 may be attached to the body so that the corresponding surface faces the region where the bladder is positioned.

In an embodiment, plural light sources included in each of the plural light source groups 114_1 to 114_4 may be configured to irradiate light of different wavelengths. Here, the plural light sources may be light emitting diodes (LEDs). Additionally, the plural light sources included in each of the plural light source groups 114_1 to 114_4 may irradiate continuous wave light.

In an embodiment, the plural photodiodes 112_1 to 112_20 may detect light to generate optical data. Specifically, the plural photodiodes 112_1 to 112_20 may detect the light intensity of diffused light being light diffused from the body. In addition, the plural photodiodes 112_1 to 112_20 may detect diffused light associated with light irradiated by light sources included in the plural light source groups 114_1 to 114_4. Additionally, each photodiode may detect diffused light and measure a voltage value corresponding to the intensity of the diffused light.

In an embodiment, the user terminal 120 may transmit an optical data detection request to the medical instrument 100. In response to the optical data detection request, the medical instrument 100 may operate the plural light source groups 114_1 to 114_4 and initiate detection operations of the plural photodiodes 112_1 to 112_20. In contrast, the medical instrument 100 may periodically detect optical data and transmit it to the user terminal 120 without receiving an optical data detection request from the user terminal 120.

In an embodiment, the medical instrument 100 may transmit multiple pieces of optical data detected through the plural photodiodes 112_1 to 112_20 to the user terminal 120. The processor included in the user terminal 120 may estimate physiological information based on the multiple pieces of optical data. Here, the physiological information may include information about water ($H_2O$), information about fat, and the like. The method of estimating physiological information based on multiple pieces of optical data will be described in detail later with reference to FIG. 4. In contrast, the medical instrument 100 may directly estimate physiological information based on the optical data without transmitting the optical data to the user terminal 120.

With this configuration, physiological information can be estimated based on optical data obtained through the medical instrument. Additionally, the estimated physiological information may be provided to the user through the user terminal. In this way, the invention according to the present disclosure may provide physiological information to the user without the help of experts such as doctors. In addition, the invention according to the present disclosure may be simple to use, have high user convenience, and be highly accessible to consumers through personalization.

Figure 2:
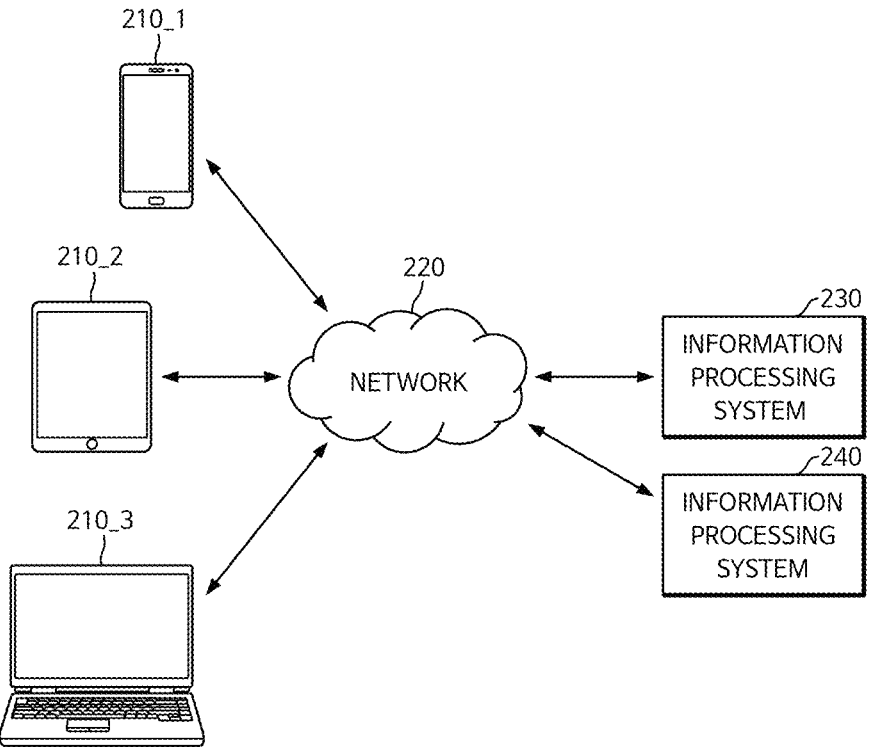
FIG. 2 is a schematic diagram showing a connected configuration that enables communication between an information processing system, a medical instrument, and a plurality of user terminals to estimate physiological information according to an embodiment of the present disclosure.

FIG. 2 is a schematic diagram showing a connected configuration that enables communication between an information processing system 230, a medical instrument 240, and a plurality of user terminals 210_1, 210_2 and 210_3 to estimate physiological information according to an embodiment of the present disclosure. As shown, the plural user terminals 210_1, 210_2 and 210_3 may be connected through a network 220 to the information processing system 230 and the medical instrument 240 that can provide a physiological information estimation service. Here, the plural user terminals 210_1, 210_2 and 210_3 may include a terminal of the user who receives a physiological information estimation service.

According to an embodiment, the information processing system 230 may include one or more server devices and/or databases that are capable of storing, providing, and executing computer-executable programs (e.g., downloadable applications) and data in association with providing a physiological information estimation service, or one or more distributed computing devices and/or distributed databases based on cloud computing services.

The physiological information estimation service provided by the information processing system 230 may be delivered to users through physiological information estimation service applications installed respectively on the plural user terminals 210_1, 210_2 and 210_3. For example, through the physiological information estimation service applications, the information processing system 230 may provide information related to physiological information estimation received from the user terminals 210_1, 210_2, 210_3 and/or the medical instrument 240 or may perform corresponding processing.

According to an embodiment, the information processing system 230 may estimate physiological information based on optical data. Here, the optical data may be data measured by the medical instrument 240. The information processing system 230 may receive optical data directly from the medical instrument 240 or may receive optical data through the user terminals 210_1, 210_2 and 210_3. The information processing system 230 may provide physiological information estimation results to the user terminals 210_1, 210_2 and 210_3 and/or the medical instrument 240.

The plural user terminals 210_1, 210_2 and 210_3 may communicate with the information processing system 230 and the medical device 240 through the network 220. The network 220 may be configured to enable communication between the plural user terminals 210_1, 210_2 and 210_3, the information processing system 230, and the medical instrument 240. Depending on the installation environment, the network 220 may be composed of, for example, a wired network such as Ethernet, wired home network (power line communication), telephone line communication or RS-serial communication, a wireless network such as mobile communication network, wireless LAN (WLAN), Wi-Fi, Bluetooth or ZigBee, or a combination thereof. There are no restrictions on communication schemes, and both communication schemes utilizing communication networks that the network 220 can include (e.g., mobile communication network, wired Internet, wireless Internet, broadcasting network, satellite network) and short-range wireless communication between the user terminals 210_1, 210_2 and 210_3 may also be included.

In FIG. 2, a mobile phone terminal 210_1, a tablet terminal 210_2, and a PC terminal 210_3 are shown as examples of user terminals; but without being limited thereto, the user terminals 210_1, 210_2 and 210_3 may be any computing device that is capable of wired and/or wireless communication and capable of installing and executing a physiological information estimation service application or a web browser. For example, user terminals may include an AI speaker, a smartphone, a mobile phone, a navigation aid, a computer, a laptop, a digital broadcasting terminal, a personal digital assistant (PDA), a portable multimedia player (PMP), a tablet PC, a game console, a wearable device, an Internet-of-things (IoT) device, a virtual reality (VR) device, an augmented reality (AR) device, and a set-top box. In addition, in FIG. 2, three user terminals 210_1, 210_2 and 210_3 are shown as communicating with the information processing system 230 and the medical instrument 240 through the network 220. But without being limited thereto, a different number of user terminals may be configured to communicate with the information processing system 230 and the medical instrument 240 over the network 220.

Figure 3:
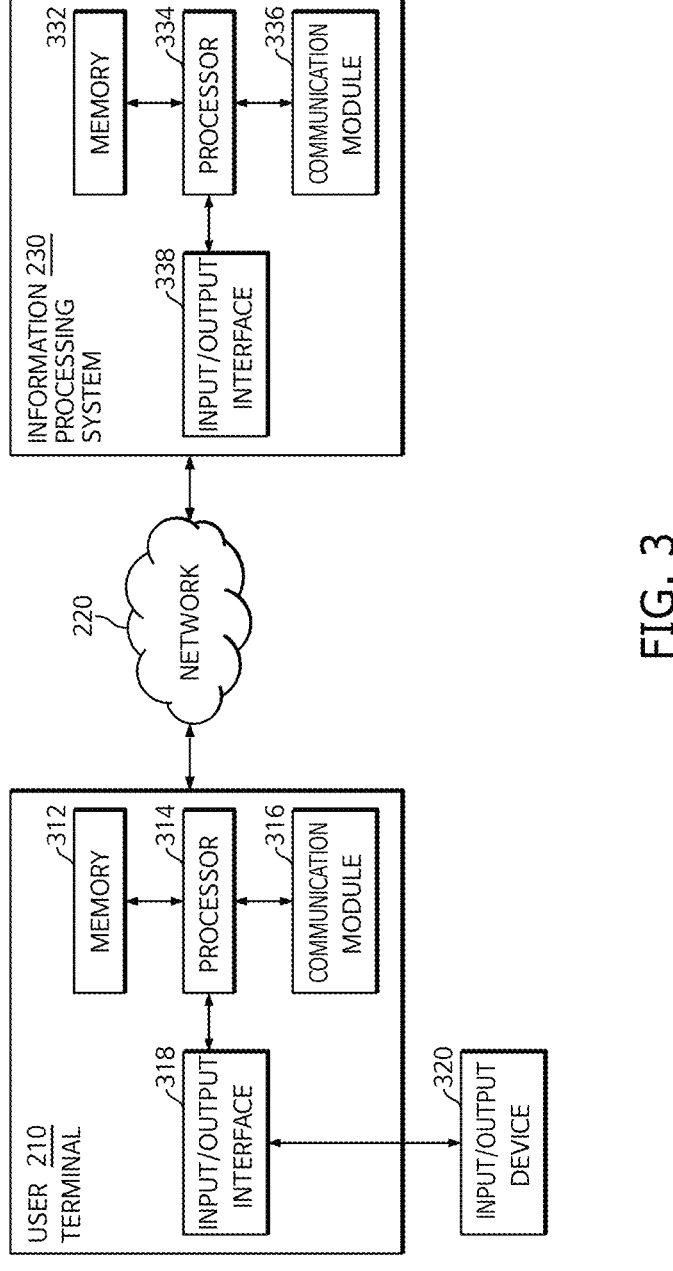
FIG. 3 is a block diagram showing the internal structure of a user terminal and an information processing system according to an embodiment of the present disclosure.

FIG. 3 is a block diagram showing the internal structure of the user terminal 210 and the information processing system 230 according to an embodiment of the present disclosure. The user terminal 210 may refer to any computing device capable of executing a physiological information estimation service application or the like and capable of wired/wireless communication, and may include, for example, the mobile phone terminal 210_1, tablet terminal 210_2, and PC terminal 210_3 in FIG. 2. As shown, the user terminal 210 may include a memory 312, a processor 314, a communication module 316, and an input/output interface 318. Similarly, the information processing system 230 may include a memory 332, a processor 334, a communication module 336, and an input/output interface 338. As shown in FIG. 3, the user terminal 210 and the information processing system 230 may be configured to communicate information and/or data through the network 220 by using their communication modules 316 and 336. In addition, the input/output device 320 may be configured to input information and/or data to the user terminal 210 through the input/output interface 318 or to output information and/or data generated from the user terminal 210.

The memory 312 or 332 may include any non-transitory computer-readable recording medium. According to an embodiment, the memory 312 or 332 may include a permanent mass storage device such as read only memory (ROM), disk drive, solid state drive (SSD), or flash memory. As another example, a permanent mass storage device such as ROM, SSD, flash memory, or disk drive may be included in the user terminal 210 or the information processing system 230 as a separate permanent storage device that is distinct from the memory. In addition, the memory 312 or 332 may store an operating system and at least one program code (e.g., code for a physiological information estimation service application installed and running on the user terminal 210).

These software components may be loaded from a computer-readable recording medium separate from the memory 312 or 332. This separate computer-readable recording medium may include a recording medium directly connectable to the user terminal 210 or the information processing system 230, and may include, for example, a computer-readable recording medium such as floppy drive, disk, tape, DVD/CD-ROM drive, or memory card. As another example, software components may be loaded onto the memory 312 or 332 through a communication module other than a computer-readable recording medium. For example, at least one program may be loaded onto the memory 312 or 332 based on a computer program installed by files provided over the network 220 by developers or a file distribution system that distributes installation files for applications.

The processor 314 or 334 may be configured to process instructions of a computer program by performing basic arithmetic, logic, and input/output operations. These instructions may be provided to the processor 314 or 334 by the memory 312 or 332 or the communication module 316 or 336. For example, the processor 314 or 334 may be configured to execute received instructions according to a program code stored in a recording device such as the memory 312 or 332.

The communication modules 316 and 336 may provide a configuration or function for the user terminal 210 and the information processing system 230 to communicate with each other through the network 220, and may provide a configuration or function for the user terminal 210 and/or the information processing system 230 to communicate with other user terminals or other systems (e.g., separate cloud system). For example, a request or data (e.g., optical data and physiological information estimation request) generated by the processor 314 of the user terminal 210 according to a program code stored in a recording device such as the memory 312 may be transmitted through the network 220 to the information processing system 230 under the control of the communication module 316. In reverse, a control signal or command provided under the control of the processor 334 of the information processing system 230 may be transmitted through the communication module 336 over the network 220 and received by the user terminal 210 through the communication module 316 of the user terminal 210.

The input/output interface 318 may be a means for interfacing with the input/output device 320. As an example, input devices may include a device such as a camera including an audio sensor and/or an image sensor, a keyboard, a microphone, or a mouse, and output devices may include a device such as a display, a speaker, or a haptic feedback device. As another example, the input/output interface 318 may be a means for interfacing with a device whose structures or functions for performing input and output are integrated into one, such as a touchscreen. For example, when the processor 314 of the user terminal 210 processes instructions of a computer program loaded onto the memory 312, a service screen or the like composed based on information and/or data provided by the information processing system 230 or another user terminal may be displayed on the display through the input/output interface 318. In FIG. 3, the input/output device 320 is shown as not being included in the user terminal 210, but without being limited thereto, it may be configured to be integrated with the user terminal 210. In addition, the input/output interface 338 of the information processing system 230 may be a means for interfacing with a device (not shown) for input or output that is capable of being connected to or included in the information processing system 230. In FIG. 3, the input/output interface 318 or 338 is shown as being configured separately from the processor 314 or 334, but without being limited thereto, the input/output interface 318 or 338 may be configured to be included in the processor 314 or 334.

The user terminal 210 or the information processing system 230 may include more components than those shown in FIG. 3. However, there may be no need to clearly show most related-art components. According to an embodiment, the user terminal 210 may be implemented to include at least some of the input/output devices 320 described above. In addition, the user terminal 210 may further include other components such as a transceiver, a global positioning system (GPS) module, a camera, various sensors, and a database. For example, if the user terminal 210 is a smartphone, it may include those components included in a typical smartphone. For example, the user terminal 210 may be implemented to further include various components such as an acceleration sensor, a gyro sensor, an image sensor, a proximity sensor, a touch sensor, an illuminance sensor, a camera module, various physical buttons, buttons using a touch panel, input/output ports, and a vibrator for vibration.

While the program for a physiological information estimation service application or the like is running, the processor 314 may receive text, image, video, voice, and/or action through input devices such as a touchscreen, keyboard, camera including an audio sensor and/or an image sensor, and a microphone connected to the input/output interface 318, and may store the received text, image, video, voice, and/or action in the memory 312 or provide the same to the information processing system 230 through the communication module 316 over the network 220.

The processor 314 of the user terminal 210 may be configured to manage, process, and/or store information and/or data received from the input/output device 320, another user terminal, the information processing system 230, and/or a plurality of external systems. The information and/or data processed by the processor 314 may be provided through the communication module 316 to the information processing system 230 over the network 220. The processor 314 of the user terminal 210 may transmit information and/or data through the input/output interface 318 to the input/output device 320 to output the same. For example, the processor 314 may display the received information and/or data on the screen of the user terminal 210.

The processor 334 of the information processing system 230 may be configured to manage, process, and/or store information and/or data received from a plurality of user terminals 210 and/or a plurality of external systems. The information and/or data processed by the processor 334 may be provided through the communication module 336 to the user terminal 210 over the network 220.

Figure 4:
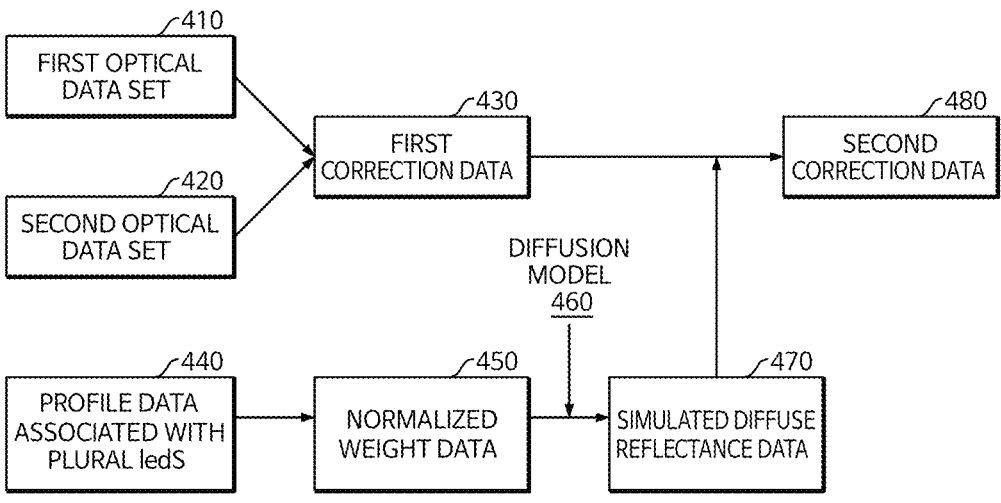
FIG. 4 is a diagram illustrating an example of a method for estimating physiological information according to an embodiment of the present disclosure.

FIG. 4 is a diagram illustrating an example of a method for estimating physiological information according to an embodiment of the present disclosure. In an embodiment, a first optical data set 410 associated with light irradiated by plural LEDs to a first substance may be received by photodiodes. Here, the photodiodes and plural LEDs may be some of the photodiodes and LEDs included in the medical instrument 100 of FIG. 1. Additionally, the first substance may be a substance (or control substance) whose reflectance information of light irradiated thereto is known in advance. Further, the first optical data set 410 may be a reference value represented by as many vectors as the number of LEDs.

In an embodiment, a second optical data set 420 associated with light irradiated by plural LEDs to a second substance may be received by photodiodes. Here, the second substance may be a test substance to be tested. For example, the second substance may include abdominal tissue, thenar tissue, or the like of the subject. Additionally, the second optical data set 420 may be a measurement value represented by as many vectors as the number of LEDs.

In an embodiment, first correction data 430 associated with the plural LEDs may be calculated based on the first optical data set 410 and the second optical data set 420. Here, the first correction data 430 may be a measurement correction value represented by as many vectors as the number of LEDs. The first correction data 430 may be expressed as Equation 2 below.

$$R = \frac{D}{C} \qquad \text{[Equation 2]}$$

Here, R may indicate the first correction data 430, D may indicate the second optical data set 420, and C may indicate the first optical data set 410. For example, if three LEDs are used, C=[C(1), C(2), C(3)], D=[D(1), D(2), D(3)], and R=[R(1), R(2), R(3)]=[D(1)/C(1), D(2)/C(2), D(3)/C(3)].

In an embodiment, normalized weight data 450 associated with plural LEDs may be calculated based on profile data 440 associated with plural LEDs. Here, the profile data 440 associated with plural LEDs may include data related to the intensity of light according to the wavelengths of the spectra of the plural LEDs. In general, LEDs radiate light of a certain band rather than light of a single wavelength, so the intensity of light for the wavelength of the LED spectrum may be not constant. Hence, the intensity of light for the wavelength of the spectrum of plural LEDs may be measured by using a spectrometer. Then, normalized weight data 450 may be calculated using Equation 3 below.

$$S_{norm} = \frac{S}{\max(S)} \qquad \text{[Equation 3]}$$

Here, $S_{norm}$ may indicate normalized weight data, S may indicate the intensity of light according to the wavelength of the LED spectrum, and max(S) may indicate the greatest intensity of light within the wavelengths of the LED spectrum. Hence, the normalized weight data 450 is the relative light intensity of each wavelength and may have a value of 0 to 1.

In an embodiment, based on the normalized weight data 450 and a diffusion model 460, simulated diffuse reflectance data 470 associated with plural LEDs may be calculated. Here, the diffusion model 460 may be a model that predicts the diffuse reflectance for the light-irradiated medium based on constants required for the diffusion model, such as chromophore concentration, extinction coefficient, refractive index, and scattering coefficient. Additionally, the simulated diffuse reflectance data 470 may be a theoretical value represented by as many vectors as the number of LEDs. The simulated diffuse reflectance data 470 may be expressed as Equation 4 below.

$$R_{sim}(j) = \Sigma_\lambda [f(N, \varepsilon, \lambda, \theta) \times S_{norm}(\lambda, j)] \qquad \text{[Equation 4]}$$

Here, $R_{sim}$ may indicate the simulated diffuse reflectance data, f may indicate the diffusion model, N may indicate the chromophore concentration, $\varepsilon$ may indicate the extinction coefficient, $\lambda$ may indicate the wavelength of the LED, and $\theta$ may indicate constants required for the diffusion model such as the refractive index and scattering coefficient. Here, the diffusion model 460 may have a constant reduced scattering of 1 mm$^{-1}$. In this way, based on the diffuse reflectance predicted by the wavelength-based diffusion model 460 and the normalized weight data 450, the simulated diffuse reflectance data 470, which is a theoretical value for each of the plural LEDs, may be calculated. For example, if three LEDs are applied, $R_{sim}$=[$R_{sim}$(1), $R_{sim}$(2), $R_{sim}$(3)].

In an embodiment, based on the first correction data 430 and the simulated diffuse reflectance data 470, the second correction data 480 may be calculated. The first correction data 430 is corrected using the first substance, but the simulated diffuse reflectance data 470 is corrected using the intensity of light according to the wavelength of the LED spectrum measured by the spectrometer, so the scale of the first correction data may be different from that of the simulated diffuse reflectance data 430. In this case, the second correction data 480 may be normalized by adjusting the scale based on a portion of the first correction data 430 and a portion of the simulated diffuse reflectance data 470. Consequently, the second correction data 480 may be expressed as Equation 5 below.

$$R_{norm} = \frac{R(1)}{R_{sim}(1)} \times R_{sim} \qquad \text{[Equation 5]}$$

Here, $R_{norm}$ may indicate the second correction data 480, R(1) may indicate the first correction data for the first LED, and $R_{sim}$(1) may indicate the simulated diffuse reflectance data for the first LED. In Equation 5, the scale is expressed as being adjusted based on the first LED, but without being limited thereto, the scale may be adjusted based on the second LED, or the like.

In an embodiment, based on the first correction data 430 and the second correction data 480, physiological information associated with the second substance may be estimated. Here, the physiological information associated with the second substance may include the concentration of chromophores in the second substance. The physiological information associated with the second substance may be estimated by using a least square method as shown in Equation 6 below.

$$N = \arg\min_{N} |R - R_{norm}(N; \theta)|^2 \qquad \text{[Equation 6]}$$

Here, N may indicate the concentration of chromophores. That is, when the square of the difference between the first correction data 430 representing the measurement correction value and the second correction data 480 representing the theoretical correction value becomes minimum, the chromophore concentration may be determined. Thus, the physiological information related to the second substance may be calculated by using Equation 7 below. Here, the physiological information may include information about water, information about fat, information about $RH_2O$, or the like.

$$H = 100 \times \frac{N_{H_2O}}{N_{H_2O} + N_{FAT}} \qquad \text{[Equation 7]}$$

Here, $NH_2O$ may indicate the water concentration in the second substance, and $N_{FAT}$ may indicate the fat concentration in the second substance.

The pseudo code of the above-described method for physiological information estimation may be represented as shown in Table 1 below.

TABLE 1

INPUT:
    D is measurement data from the photodiode for each LED
    C is calibration data for the photodiode for each LED
    S are the LED spectral measurements
    ε are the chromophore extinction coefficients for all wavelengths
    λ are the wavelengths for extinction coefficients
    N are the chromophore concentrations
    f is the steady-state diffusion model function
    θ are all other diffusion model inputs (e.g., index of refraction,
      scattering, etc.)
OUTPUT:
    H is the calculated hydration ratio
START:
    1. CALIBRATE measurement data D using calibration data C $$R = \frac{D}{C}$$

2. NORMALIZE spectral information of the LEDs S $$S_{Norm} = \frac{s}{\max(S)}$$

3. FIT to solve for chromophore concentration N $$N = \underset{N}{\arg\min} |R - R_{Norm}(N; \theta)|^2$$

WHERE:
      FOR j = 1 to length of R
    $R_{sim}(j) = \Sigma_\lambda [f(N, \varepsilon, \lambda, \theta) \times S_{Norm}(\lambda, j)]$
      END $$R_{Norm} = R(1) \times \frac{R_{sim}}{R_{sim}(1)}$$

TABLE 1-continued

4. RETURN final output H $$H = 100 \times \frac{N_{H2O}}{N_{H2O} + N_{FAT}}$$

With this configuration, crosstalk can be reduced by more accurately estimating physiological information while using multi-wavelength LEDs and photodiodes. Hence, it is possible to promote simplification and miniaturization of spectroscopy technology. In addition, the method of the present disclosure may be usefully applied to narrow-band LED-based devices such as wearable hydration monitors.

Figure 5:
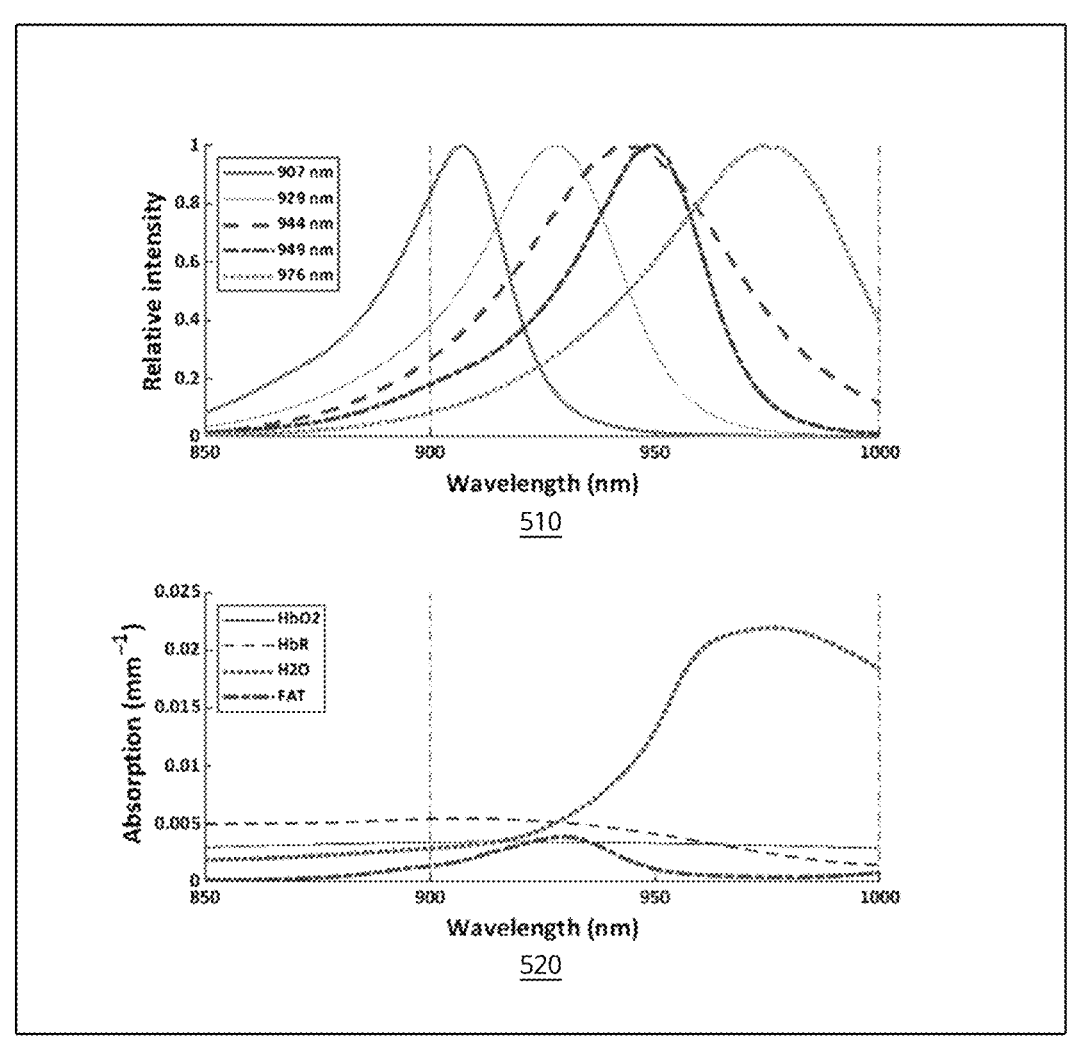
FIG. 5 is a diagram showing examples of an LED spectrum and chromophore absorption spectrum an according to an embodiment of the present disclosure.

FIG. 5 is a diagram showing an example of the LED spectrum and chromophore absorption spectrum an according to an embodiment of the present disclosure. The first graph 510 is an example showing the LED spectrum. To apply the nb-DRS method of the present disclosure, five LEDs with a spectrum as shown in the first graph 510 may be used. Here, the peak wavelengths of the LEDs may be 907 nm, 929 nm, 944 nm, 949 nm, and 976 nm, respectively, and the FWHMs of the LEDs may be 29 nm, 38 nm, 56 nm, 35 nm, and 53 nm, respectively. Additionally, in the first graph 510, the vertical dotted line may represent the wavelength analysis region of nb-DRS, and the LEDs may be labeled and displayed according to their peak wavelengths. Further, the vertical axis of the first graph 510 may represent the relative light intensity of each LED according to the normalized weight data described above in FIG. 4.

The second graph 520 is an example showing the chromophore absorption spectrum of human breast tissue containing 12.6 μM of oxyhemoglobin (HbO2), 27.9 μM of deoxyhemoglobin (HbR), 45.1 percent of water ($H_2O$), and 29.8 percent of fat (FAT). Compared to the typical absorption spectrum of tissue containing chromophores of oxyhemoglobin, deoxyhemoglobin, water, and fat as shown in the second graph 520, the spectrum of the LEDs used in this disclosure may be wide enough to overlap not only the absorption peaks of fat and water in the wavelength analysis region of nb-DRS, but also between the LEDs. In particular, the spectrum of 944 nm, 949 nm, and 976 nm LEDs may be wide enough to overlap the absorption peaks of fat and water.

Figure 6:
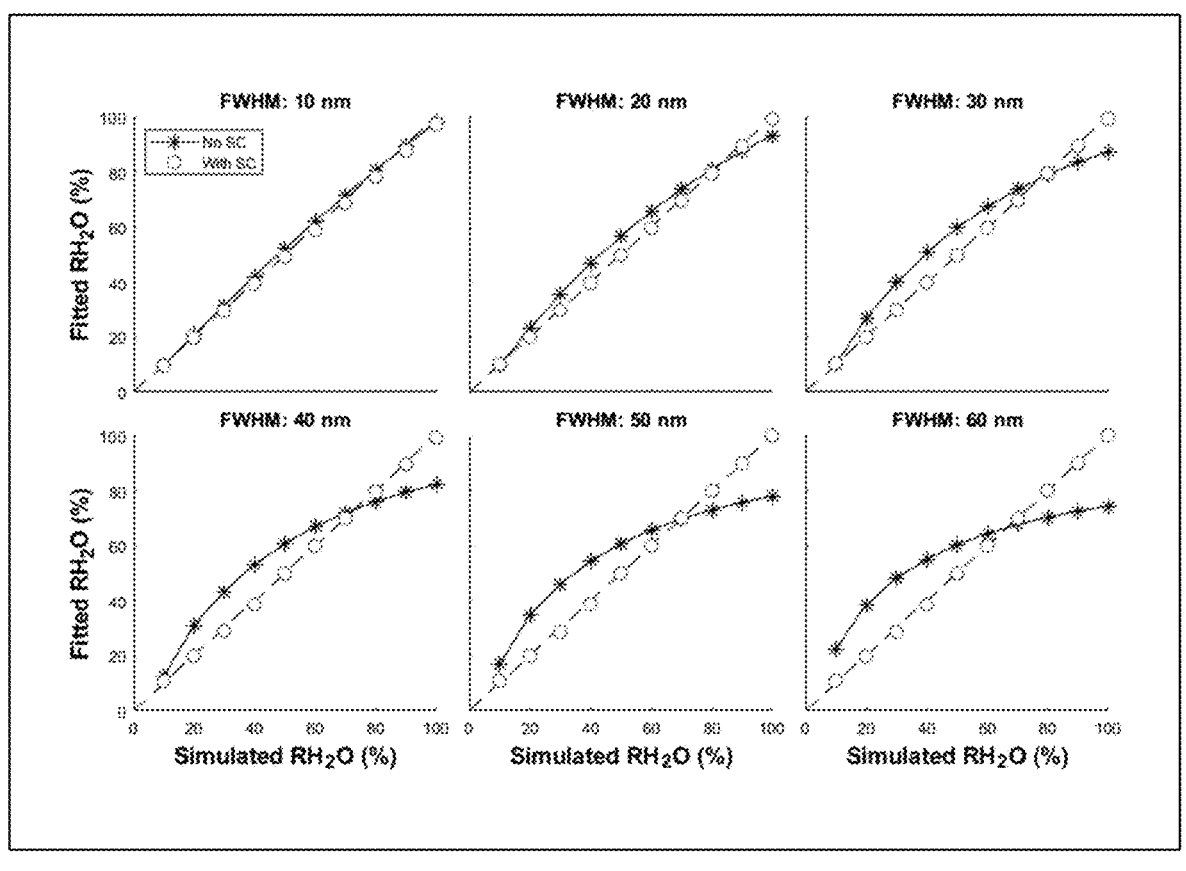
FIG. 6 is a diagram showing examples of simulation results according to an embodiment of the present disclosure.

FIG. 6 is a diagram showing an example of simulation results according to an embodiment of the present disclosure. The graphs shown in FIG. 6 show an example of simulation results of estimating physiological information (e.g., $RH_2O$) in cases where the spectral correction method (or SC) of the present disclosure is applied and is not applied. Here, dotted lines may represent an identity line. In addition, when the spectral correction method is not applied, the wavelength of each LED can be assumed to be the peak wavelength.

A set of simulated broadband reflectance spectra may be generated by using a steady-state diffusion model with various $RH_2O$ values and a constant reduced scattering of 1 mm$^{-1}$. Here, the diffusion model may be a model that predicts the diffuse reflectance of a light-irradiated medium based on the chromophore concentration and extinction coefficient. LED profiles with wavelengths equal to the center wavelength of the device may be simulated as Gaussian curves with FWHM values increasing from 10 nm to 60 nm. Then, the simulated broadband reflectance may be transformed into simulated LED reflectance by using Gaussian curves.

As shown in FIG. 6, as the spectrum width (or FWHM) of the LED increases, the error between the simulation results estimating physiological information when the spectral correction method is applied and when the spectral correction method is not applied may gradually increase. Specifically, the reflectance spectrum shown in FIG. 6 may be simulated by using LEDs whose FWHM ranges from 10 nm to 60 nm. Then, physiological information may be estimated by applying nb-DRS to both cases of with and without using the spectral correction method. As shown, when the FWHM of the LEDs is 10 nm, compared to the identity line, the performances of the cases with and without applying the spectral correction method may be similar with an error range of less than 1 percent. However, as the FWHM of the LEDs increases, the error between the case where the spectral correction method is applied and the case where the spectral correction method is not applied may gradually increase. For example, when the FWHM of the LEDs is 60 nm, the average absolute error between the estimated value of physiological information and the identity line may jump to 13.4 percent in the case of not applying the spectral correction method. On the other hand, when the spectral correction method is applied, the estimated value of physiological information can be maintained at the same level of accuracy (less than 1 percent) for all simulated FWHMs of the LEDs.

Figure 7:
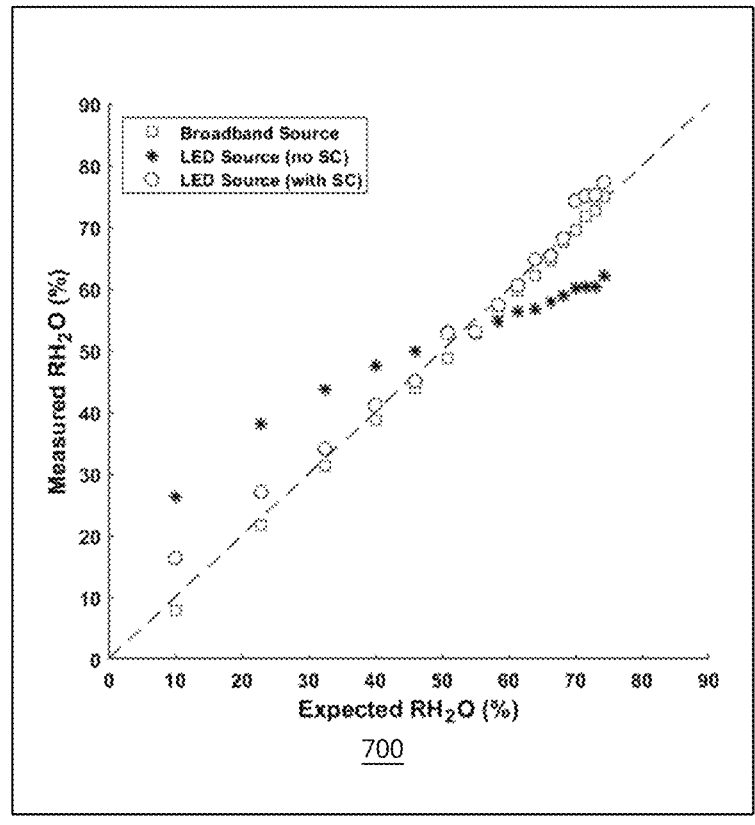
FIG. 7 is a diagram showing an example of emulsion phantom results according to an embodiment of the present disclosure.

FIG. 7 is a diagram showing an example of emulsion phantom results according to an embodiment of the present disclosure. The graph 700 shown in FIG. 7 illustrates the results of the emulsion phantom measurement performed by nb-DRS for the cases of using a broadband light source, using LEDs without application of the spectral correction method, and using LEDs with application of the spectral correction method. Here, the dotted line may represent an identity line, and the emulsion phantom may be the first substance (or, control substance) described above in FIG. 4. The dilution volume added at each step was maintained at 100 ml, but the total volume of the emulsion phantom increased over time. As a result, a nonlinear dilution trend may be identified in which $RH_2O$ increases more at the beginning of the emulsion phantom experiment and $RH_2O$ changes less as it approaches the end of the experiment.

An emulsion phantom may be constructed with minor modifications to maintain the phantom in liquid form instead of a solid gelatin. An oil and water emulsion phantom may be fabricated by adjusting the initial oil to water ratio to 90:10 using soy lecithin (2% by weight) as the emulsifier. Then, the solutions may be mixed using a high-speed vacuum blender. Next, the phantom may be diluted by adding 100 mL of water at each step. By maintaining water as a continuous medium, the phantom may be diluted without separation of its constituents. By using this approach, a wide range of phantom $RH_2O$ values may be measured without the need to construct a new phantom for each step. After going through a 15-step dilution process, the final expected $RH_2O$ may be 74.3 percent. After every step, the phantom may be homogenized using a hand-held mixer.

As shown by the graph 700, the spectral correction method may be tested by comparing the three approaches using an emulsion phantom. First, the approach using a broadband light source and spectrometer detector may perform most accurately with an average and standard deviation error of 1.4±0.7 percent. In this case, the maximum error may correspond to 2.2 percent.

Next, for the approach using LEDs and photodiode detectors, the effects of spectral crosstalk may be recognized not only by accuracy but also by sensitivity. For example, the LED at 929 nm may be considered sensitive to fat because its peak wavelength coincides with the lipid absorption peak. However, in reality, due to the wide spectral bandwidth of the LED, both water and fat may affect reflectance measurements using this LED. This may mean that the dynamic range is poor if the spectral correction method of the present disclosure is absent. These points may be confirmed in simulations and emulsion phantom experiments. If the spectral correction method is not applied, the error on the phantom emulsion may correspond to 8.7±4.4 percent with a maximum error of 14.1 percent.

Finally, when the spectral correction method is applied by using the same dataset, the error on the phantom emulsion may be improved to 2.2±1.7 percent with a maximum error of 6.4 percent. In addition, when the spectral correction method is applied, it may be confirmed that the sensitivity is restored with a slope comparable to that of the approach using a broadband light source.

Figure 8:
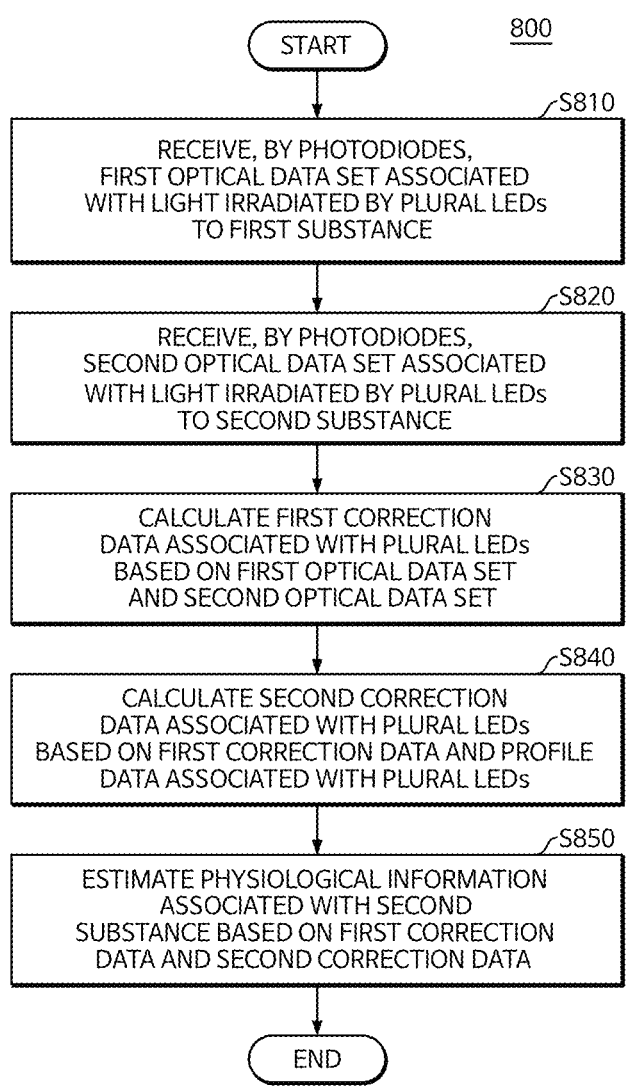
FIG. 8 is a flowchart showing an example of a method according to an embodiment of the present disclosure.

FIG. 8 is a flowchart illustrating an example of the method 800 according to an embodiment of the present disclosure. In an embodiment, the method 800 may be performed by at least one processor. The method 800 may begin with receiving, by the processor through photodiodes, a first optical data set associated with light irradiated by plural LEDs to a first substance (S810). Here, the first substance may be a substance whose reflectance information of light irradiated to it is known in advance.

Thereafter, the processor may receive, through the photodiodes, a second optical data set associated with light irradiated by the plural LEDs to a second substance (S820). Here, the second substance may be a test substance to be tested. In addition, the processor may calculate first correction data associated with the plural LEDs based on the first optical data set and the second optical data set (S830).

Thereafter, the processor may calculate second correction data associated with the plural LEDs based on the first correction data and profile data associated with the plural LEDs (S840). Specifically, the processor may calculate normalized weight data associated with the plural LEDs based on the profile data associated with the plural LEDs. In addition, the processor may calculate simulated diffuse reflectance data associated with the plural LEDs based on the normalized weight data and a diffusion model. Here, the diffusion model may be a model that predicts the diffuse reflectance of a light-irradiated medium based on the chromophore concentration and extinction coefficient. Additionally, the processor may calculate the second correction data based on the first correction data and simulated diffuse reflectance data associated with the plural LEDs. Additionally or alternatively, the processor may calculate the second correction data by adjusting the scale of the simulated diffuse reflectance data based on a portion of the first correction data and a portion of the simulated diffuse reflectance data.

Thereafter, the processor may estimate physiological information associated with the second substance based on the first correction data and the second correction data (S850). Here, the physiological information may include information about water ($H_2O$) and information about fat.

Measurements of physiological information were performed on two healthy human subjects (31-year-old male and 30-year-old female). Abdomen and thenar sites may be representative examples of fatty tissue and lean tissue, respectively. That is, the abdomen tissue and the thenar tissue may be the second substance described above in FIG. 4. In this case, the light source-detector distance for the LED and photodiode combination may be shortened to improve the signal-to-noise ratio. The source-detector separation for the LED and photodiode combination was shortened to 11 mm to improve the signal-to-noise ratio. Hemoglobin may be included during chromophore fitting.

As shown in Table 2 illustrating the results of experiments on human tissues of two subjects, the present disclosure may clearly distinguish between abdomen tissue and thenar tissue of the human body, like the approach using a broadband light source. Because there is a lot of fat in abdomen tissue, $RH_2O$ on abdomen tissue may be low, ranging from 18.9 to 37.8 percent for the approach using a broadband light source, and ranging from 22.7 to 37.8 percent for the approach using LEDs with application of the spectral correction method.

In contrast, as can be seen from the results of the approach using a broadband light source, thenar tissue may be a much leaner tissue with $RH_2O$ of about 77 percent. For the approach using LEDs with application of the spectral correction method, a range between 69 percent and 80.7 percent may be identified. This discrepancy may be caused by slightly different volume measurements due to differences in source-detector separation (15 mm versus 11 mm). In both of the two approaches, the two tissue types may be clearly distinguished, with abdomen tissue having a much lower $RH_2O$ than thenar tissue.

However, if the spectral correction method is not applied, the two tissue types may be not clearly distinguished. Whereas only water and fat are contained in phantom emulsion experiments, live human tissue contains hemoglobin factors, which may exacerbate spectral crosstalk errors. Likewise, complex tissues may be computationally more challenging due to the presence of other factors such as hemoglobin, and unaccounted chromophores. In this case, accuracy may be improved by adding more LEDs and including other chromophores such as myoglobin or melanin.

TABLE 2

| Tissue | Broadband | LED(with SC) | LED(no SC) |
|---|---|---|---|
| Abdomen 1 | 37.8% | 37.8% | 58.2% |
| Abdomen 2 | 18.9% | 22.7% | 53.6% |
| Thenar 1 | 75.0% | 80.7% | 60.6% |
| Thenar 2 | 78.7% | 69.0% | 59.7% |

The present disclosure provides a method for increasing the accuracy of $RH_2O$ measurement using nb-DRS, despite using LEDs with broad overlapping spectra in a narrow wavelength region. Specifically, the accuracy of $RH_2O$ measurement may be increased by using the already known spectrum of LEDs for chromophore calculation. These results may be confirmed through simulations, emulsion phantoms, and experiments in human tissue using nb-DRS. The present disclosure may facilitate simplification and miniaturization of spectroscopic technology and may be particularly useful in narrowband LED-based devices.

The above-described method may be provided as a computer program stored in a computer-readable recording medium for execution on a computer. Media may be used to continuously store programs executable on a computer or to temporarily store them for execution or download. Additionally, the media may be a variety of recording or storage means in the form of a single piece of hardware or a combination of several pieces of hardware, and the media may be directly connected to a certain computer system or may be distributed over a network. Examples of the media may include magnetic media such as a hard disk, floppy disk and magnetic tape, optical recording media such as CD-ROM and DVD, magneto-optical media such as floptical disk, ROM, RAM, flash memory, which may be configured to store program instructions. Additionally, examples of other media may include recording or storage media managed by app stores that distribute applications, or by sites or servers that supply or distribute various other software.

The methods, operations, or techniques of the present disclosure may be implemented with various means. For example, these techniques may be implemented in hardware, firmware, software, or a combination thereof. Those skilled in the art will understand that the various illustrative logical blocks, modules, circuits, and algorithm steps described in connection with the present disclosure may be implemented in electronic hardware, computer software, or a combination thereof. To clearly illustrate this mutual replacement between hardware and software, various illustrative components, blocks, modules, circuits, and steps have been described above generally in terms of their functionality. Whether such functionality is implemented in hardware or software depends on the specific application and design requirements imposed on the overall system. Those skilled in the art may implement the described functionality in various ways for specific applications, but such implementations should not be construed as departing from the scope of the present disclosure.

In hardware implementation, the processing units used to perform the techniques may be implemented with one or more ASICs, DSPs, digital signal processing devices (DSPDs), programmable logic devices (PLDs), field programmable gate arrays (FPGAs) s), processors, controllers, microcontrollers, microprocessors, electronic devices, other electronic units designed to perform the functions described in this disclosure, computers, or a combination thereof.

Thus, the various example logical blocks, modules, and circuits described in connection with the present disclosure may be implemented with or performed by general-purpose processors, DSPs, ASICs, FPGAs, programmable logic devices, discrete gates, transistor logics, discrete hardware components, or any combination thereof designed to perform the functions described herein. A general-purpose processor may be a microprocessor, but alternatively, the processor may be any conventional processor, controller, microcontroller, or state machine. The processors may also be implemented as a combination of computing devices, such as a DSP and a microprocessor, a plurality of microprocessors, one or more microprocessors in conjunction with a DSP core, or any other configurations.

In firmware and/or software implementation, the techniques may be implemented as instructions stored in a computer-readable medium such as random access memory (RAM), read-only memory (ROM), non-volatile random access memory (NVRAM), programmable read-only memory (PROM), erasable programmable read-only memory (EPROM), electrically erasable PROM (EEPROM), flash memory, compact disc (CD), or magnetic or optical data storage device. The instructions may be executable by one or more processors, and may cause the processor(s) to perform certain aspects of the functionality described in the present disclosure.

When implemented in software, the techniques may be stored in or transmitted through computer-readable media as one or more instructions or code. The computer-readable media include both computer storage media and communication media by including any media that facilitate transfer of a computer program from one place to another. The storage media may be any available media that can be accessed by a computer. By way of non-limiting examples, these computer readable media may include RAM, ROM, EEPROM, CD-ROM or other optical disk storage, magnetic disk storage or other magnetic storage devices, or any other media that may be used to transport or store desired program codes in the form of instructions or data structures and may be accessed by a computer. In addition, random access may be suitably made to computer-readable media.

For example, if software is transmitted from a website, server, or other remote source by using coaxial cable, fiber optic cable, twisted pair cable, digital subscriber line (DSL), or wireless technologies such as infrared ray, radio wave, and microwave, these coaxial cable, fiber optic cable, twisted pair cable, digital subscriber line, or wireless technologies such as infrared ray, radio wave, and microwave may be included in the definition of media. As used herein, disks and discs include CD, laser disc, optical disc, digital versatile disc (DVD), floppy disk, and Blu-ray disc, where disks usually reproduce data magnetically, whereas discs reproduce data optically using lasers. Combinations of the above ones should also be included in the scope of computer-readable media.

Software modules may be configured to reside in RAM memory, flash memory, ROM memory, EPROM memory, EEPROM memory, registers, hard disk, removable disk, CD-ROM, or any other form of well-known storage medium. An exemplary storage medium may be coupled to a processor so that the processor may read information from or write information to the storage medium. The processor and storage medium may be present within an ASIC. The ASIC may be present in a user terminal. Alternatively, the processor and storage medium may be present as separate components in the user terminal.

Although the above-described embodiments have been described as utilizing aspects of the subject matter disclosed herein on one or more standalone computer systems, the disclosure is not limited thereto and may also be implemented in conjunction with any computing environment such as a network or distributed computing environment. Furthermore, aspects of the subject matter of this disclosure may be implemented with multiple processing chips or devices, and storage may be similarly effected across the multiple devices. These devices may include PCs, network servers, and portable devices.

Although the present disclosure has been described in relation to some embodiments in this specification, various modifications and changes may be made without departing from the scope of the present disclosure as can be understood by those skilled in the art to which the invention pertains. In addition, such modifications and changes should be considered to fall within the scope of the claims attached herein.

What is claimed is:

1. A medical device configured to be attached to a human body surface, the medical device comprising:
a plurality of light emitting diodes (LEDs) disposed on a surface of the medical device and facing the human body surface, wherein the plurality of LEDs are configured such that:
a first LED and a second LED of the plurality of LEDs are configured to emit a first wavelength; and
a third LED and a fourth LED of the plurality of LEDs are configured to emit a second wavelength;
a plurality of photodiodes disposed on the surface of the medical device and facing the human body surface, wherein each of the plurality of photodiodes is configured to receive optical data related to the human body surface;
a communication interface;
a memory; and
at least one processor coupled to the memory and configured to execute at least one computer-readable program stored in the memory, wherein the at least one computer-readable program includes instructions that, when executed by the at least one processor, cause the medical device to:
store a first optical data set corresponding to measurements of reflected light from a first substance with known reflectance information;
cause the plurality of LEDs to emit a plurality of wavelengths of light towards the human body surface;
receive, via the plurality of photodiodes and while the plurality of LEDs emit the plurality of wavelengths, a second optical data set corresponding to measurements of reflected light from tissue of the human body surface;
determine, based on a ratio of each portion of the second optical data set corresponding to a particular LED of the plurality of LEDs and a corresponding portion of the first optical data set corresponding to the particular LED, first correction data;
determine, based on the first correction data and profile data indicating an intensity of each LED of the plurality of LEDs, second correction data;
estimate, based on the first correction data and the second correction data, physiological information associated with a composition of the tissue of the human body surface; and
transmit, to a second computing device and via the communication interface, data indicating the composition of the tissue of the human body surface.

2. The medical device of claim 1, wherein each of the plurality of LEDs is positioned next to a corresponding photodiode of the plurality of photodiodes.

3. The medical device of claim 1, wherein a distance between each of the plurality of LEDs and the corresponding diode is about 11 mm.

4. The medical device of claim 1, wherein the first substance with known reflectance information comprises an oil and water emulsion.

5. The medical device of claim 1, wherein the instructions, when executed by the at least one processor, cause the medical device to determine the second correction data by causing the medical device to:
simulate, for each of the plurality of LEDs, diffuse reflectance data; and
compare, for each of the plurality of LEDs, a portion of the first optical data corresponding to a particular LED with a corresponding portion of the simulated diffuse reflectance data.

6. The medical device of claim 5, wherein the instructions, when executed by the at least one processor, cause the medical device to calculate the simulated diffuse reflectance data based on an extinction coefficient of the tissue.

7. The medical device of claim 5, wherein the instructions, when executed by the at least one processor, cause the medical device to calculate the simulated diffuse reflectance data based on a wavelength of each of the plurality of LEDs.

8. The medical device of claim 5, wherein the instructions, when executed by the at least one processor, cause the medical device to calculate the simulated diffuse reflectance data based on a scattering coefficient.

9. The medical device of claim 1, wherein the instructions, when executed by the at least one processor, cause the medical device to cause the plurality of LEDs to emit the plurality of wavelengths of light towards the human body surface by causing the medical device to:

receive, via a network and from the second computing device, an optical data detection request; and cause, based on the optical data detection request, the plurality of LEDs to emit the plurality of wavelengths.

10. The medical device of claim 1, wherein the data indicating the composition of the tissue of the human body surface indicates tissue fat content.

11. The medical device of claim 1, wherein the data indicating the composition of the tissue of the human body surface indicates tissue water content.

12. The medical device of claim 1, wherein each of the plurality of LEDs are configured to emit continuous wave light.

13. The medical device of claim 1, wherein the human body surface corresponds to an approximate location of a human bladder.

\* \* \* \* \*